United States Patent [19]

Gyure et al.

[11] 4,300,678
[45] Nov. 17, 1981

[54] SYRINGE PACKAGE WITH EVIDENCE OF OPENING

[75] Inventors: Sandor Gyure, West Orange; Joseph M. Szwarc, Cedar Grove, both of N.J.

[73] Assignee: Becton, Dickinson and Company, Paramus, N.J.

[21] Appl. No.: 137,936

[22] Filed: Apr. 7, 1980

[51] Int. Cl.³ .............................................. B65D 83/10
[52] U.S. Cl. .................................. 206/364; 128/224
[58] Field of Search ................. 206/364, 365, 366; 128/224

[56] References Cited

U.S. PATENT DOCUMENTS

| | | | |
|---|---|---|---|
| 3,008,570 | 11/1961 | Roehr et al. | 206/364 |
| 3,074,541 | 1/1963 | Roehr | 206/364 |
| 3,865,236 | 2/1975 | Rycroft | 206/364 |
| 3,893,608 | 7/1975 | Koenig | 206/364 |

Primary Examiner—Joseph Man-Fu Moy
Attorney, Agent, or Firm—Richard J. Rodrick

[57] ABSTRACT

A syringe package includes a hollow barrel and a slidable plunger inside the barrel extending out of its proximal end. A needle cannula extends from a distal end of the barrel. A shield covers the cannula and is connected to the barrel to provide a seal thereto. The shield has a frangible portion adapted to be ruptured so that a first portion of the shield is removable and a second portion remains connected to the barrel as evidence of a broken seal. A cap covers the proximal end of the plunger and is connected to the barrel to provide a seal. The cap has a frangible portion adapted to be ruptured so that a first portion of the cap is removable and a second portion is adapted to remain connected to the barrel as evidence of a broken seal at this end of the syringe.

10 Claims, 5 Drawing Figures

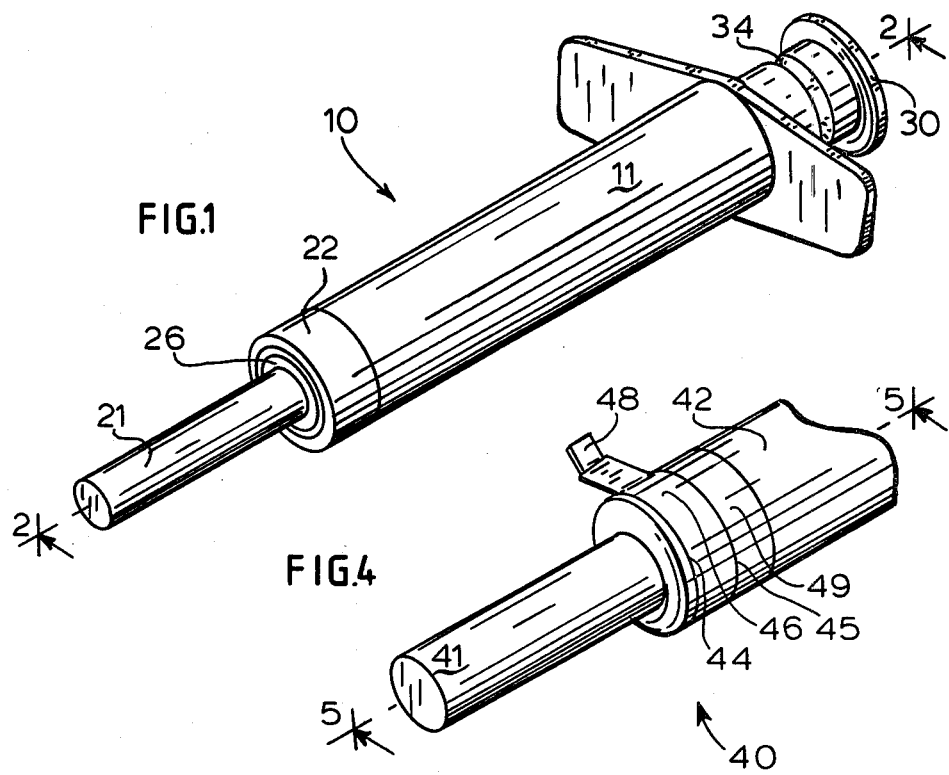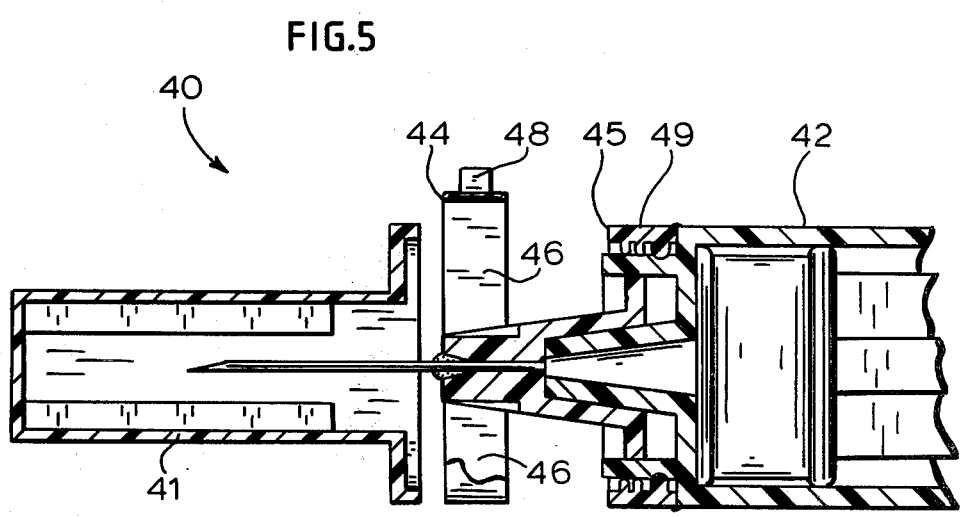

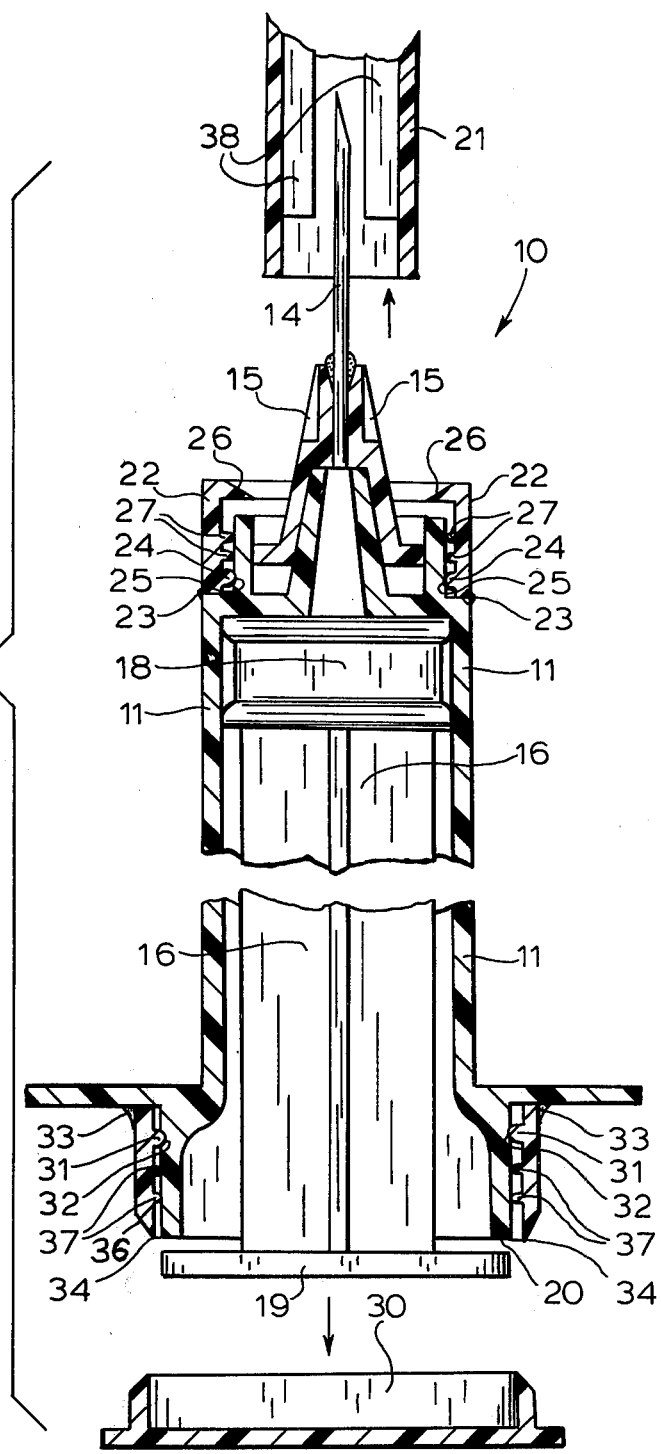

SYRINGE PACKAGE WITH EVIDENCE OF OPENING

BACKGROUND OF THE INVENTION

The present invention relates to a packaged article usually meant to be sterile or clean, and more particularly concerns a packaged syringe which includes evidence that the package seal has been broken so that the user knows that its sterility or cleanliness has been compromised.

Clean or sterile articles particularly useful for medical applications are packaged to preserve this sterility. The packages for these articles are intended to provide a bacteria barrier to prevent bacteria from entering inside the package to contaminate its contents. In most instances, the package is opened immediately prior to using a sterile article such as a syringe so as to minimize the time period which the sterile article is exposed. There are, however, instances when a clean or sterile article may be removed from its barrier package and, perhaps not be used at the time of initial opening. For this and a variety of other reasons, users of these sterile articles are often able to reassemble the syringe or like device back into the package from which it was removed. Upon this reassembly, however, no resterilization technique is performed so that the article may be exposed to a contamination path for an extended period of time. When either the same user or another user attempts to use this previously opened medical article, it may not be possible to tell whether or not it had been opened once before. In this event, the user may presume that the article is still sterile, if there is no knowledge that the package had been previously opened. On the other hand, the opposite conclusion should have been arrived at, namely, that the previously opened article would indicate that sterility has been compromised and that the article is no longer clean for its intended use. Therefore, a clear mechanism to establish evidence that a packaged sterile article has been opened is a desired feature in the use of these kinds of articles.

In U.S. Pat. Nos. 3,333,682; 3,272,322 and 2,884,123, medical devices are described which include some evidence that the sterile article has been previously removed from the package. However, in those patents, the container itself is broken with no evidence remaining upon the originally contained article that the article has been removed from a clean or sterile package. In U.S. Pat. No. 4,181,223, a syringe is completely coated with a film that is broken at the cap end or the plunger end by the user just before use. Although portions of the broken film remain attached to the syringe barrel after the seal is broken, the application of the film to the entire syringe assembly can be overly complicated, expensive and difficult to manage. In this case, when the user merely has the article itself in hand, it cannot be ascertained whether or not that article has been used previously or perhaps otherwise presumed contaminated. Accordingly, it can be seen that there is still a strong need for positive evidence in conjunction with sterile articles such as syringes and the like that they have been removed from the original package to thereby serve as an unequivocal indication that sterility or cleanliness has been compromised.

SUMMARY OF THE INVENTION

A syringe package of the present invention comprises a hollow barrel and slidable plunger means inside the barrel extending out of a proximal end thereof. A needle cannula extends from a distal end of the barrel in fluid communication with the interior of the barrel. A shield covers the cannula and is connected to the barrel to provide a seal thereto. Frangible means associated with the shield is adapted to be ruptured so that the shield is removable to expose the cannula. Indicator means remains connected to the barrel as evidence of a broken seal. A removable cap covers the proximal ends of the plunger means and is preferably connected to the barrel to provide a seal thereto. In the preferred embodiment, this cap has frangible means adapted to be ruptured so that a first portion of the cap is removable to expose the plunger means. A second portion of the cap is adapted to remain connected to the barrel as evidence of a broken seal. The shield, cap and barrel exterior provide a package for the syringe.

In a preferred embodiment of the present invention, the barrel of the syringe is plastic and so are both shield and cap covering the respective ends of the syringe barrel. Both the shield and the cap have frangible portions which are areas of reduced wall thickness relative to the wall thickness of the remaining portions of those components. The breaking stress of these reduced thickness wall portions is less than the bond strength of the connection between the shield and the cap to the barrel so that the respective second portions of shield and cap can remain connected to the barrel after rupture.

In another embodiment of the present invention, the frangible portion of the shield or the cap is a peelable section of material between the first and the second portions thereof which operates to separate those portions for removal of the first portion.

In accordance with the principles of the present invention, the structure of the package is notably different from previously known structures intended for similar functions. In particular, when the cannula shield and the plunger cap are removed from respective ends of the syringe barrel, a portion remains connected to the barrel. This provides any user of this article with clear evidence that the original seal has been broken so that sterility or cleanliness has been compromised. Any user of this article who finds a loosely reattached shield or cap can then quickly presume that the enclosed syringe is no longer clean or sterile. Any attempts to reassemble the shield or cap will result in only a loose connection since the two portions cannot be rejoined in integral fashion after the original rupture of the seal has been made. Thus, the present invention offers the advantage to the user of the quick, clear indication to the user as to whether or not the original seal at either end of the syringe has been broken. Furthermore, the syringe of the present invention is packaged without the use of a package or film completely surrounding the entire syringe. Specifically, the cannula shield, the plunger cap and the outside periphery of the syringe barrel together combine to form the package for the assembly. Cleanliness or sterility of the syringe is provided by the seal of the shield and the cap to the syringe barrel. This packaged assembly is compact, smaller in size and weight than more bulky package assemblies and convenient to manufacture and use.

BRIEF DESCRIPTION OF THE DRAWINGS

FIG. 1 is a perspective view of a preferred embodiment of a syringe package of the present invention;

FIG. 3 is a cross-sectional view of the embodiment of FIG. 1 illustrating the removal of shield and cap portions of the package;

FIG. 4 is a fractionalized perspective view of the distal end of the syringe package illustrating an alternate embodiment of the frangible portion of the cannula shield; and FIG. 5 is an enlarged cross-sectional view taken along 5—5 of FIG. 4 illustrating the separation of the portions of the cannula shield.

DETAILED DESCRIPTION

Figure 2:
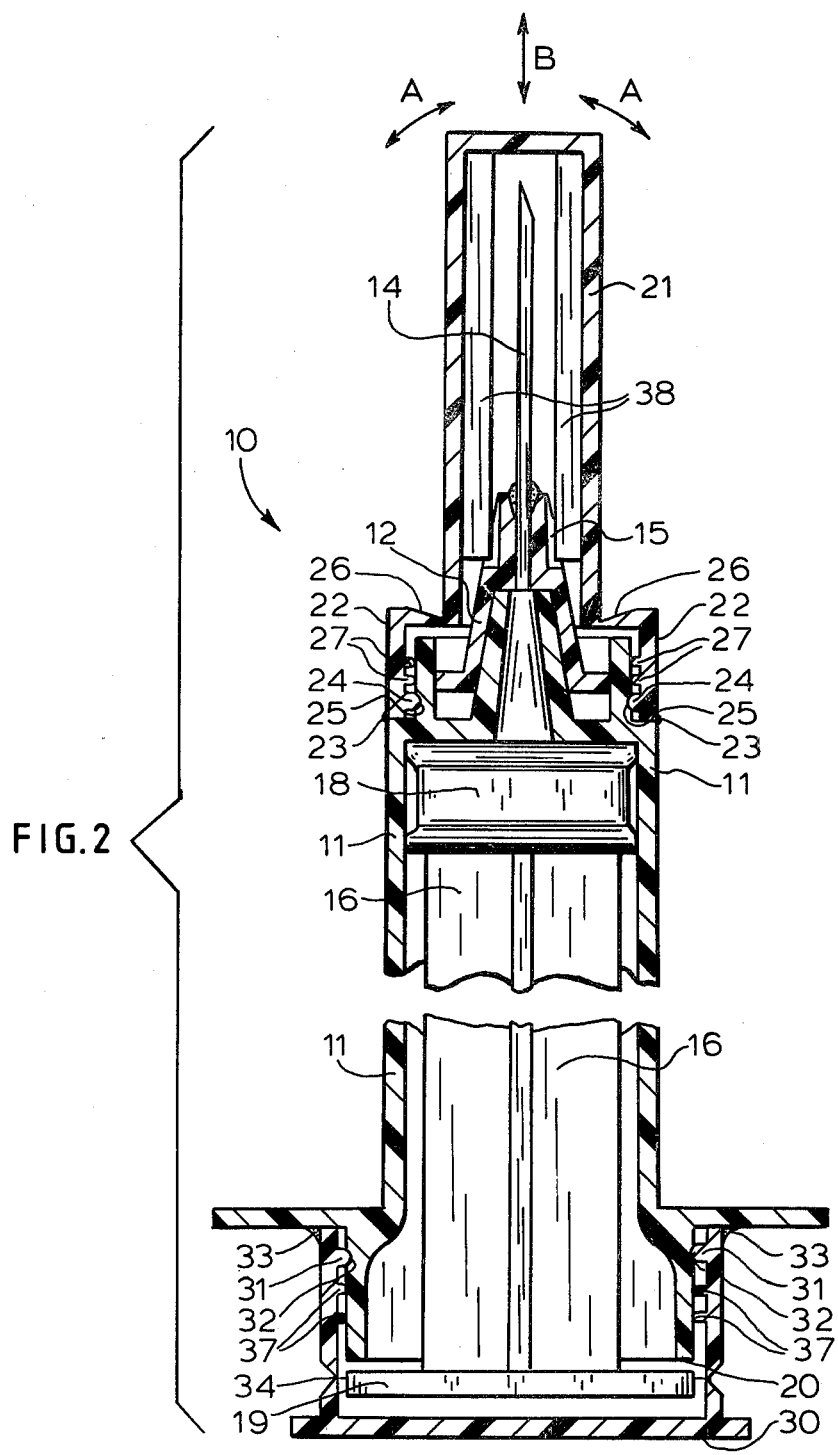
FIG. 2 is a cross-sectional view taken along 2—2 of FIG. 1.

While this invention is satisfied by embodiments in many different forms, there is shown in the drawings and will herein be described in detail preferred embodiments of the invention, with the understanding that the present disclosure is to be considered as exemplary of the principles of the invention and is not intended to limit the invention to the embodiments illustrated. The scope of the invention will be pointed out in the appended claims.

Turning to the drawings, particularly FIGS. 1 and 2, there is shown a hypodermic syringe generally indicated as 10 of a type known in the art. As known in this art, syringe 10 is comprised of an elongated, hollow barrel 11 and a hub 12 having connected thereto a needle cannula 14 extending from a distal end of the barrel in fluid communication with the interior of the barrel. In the embodiment being described, hub 12 includes one or more longitudinally extending ribs 15, the purpose of which will be described hereinafter. A slidable plunger 16 is inserted inside barrel 11 with its fluid-tight piston 18 facing the distal end of the barrel and a thumb disk 19 or the like extending out of a proximal end of the barrel. Preferably, plunger 16 and barrel are of such comparative lengths so that when the plunger is seated all the way into the barrel thumb disk 19 approaches proximal edge 20 at that end of the barrel. Such hypodermic syringes are conventional in the art and one skilled in this art would appreciate that no further details of the syringe are needed for a complete understanding of the present invention.

Covering the needle cannula is a shield 21. This shield is preferably an integral piece which not only covers needle cannula 14 but is adapted to be sealably connected to the distal end of barrel 11 over hub 12. There are many ways to provide this connection of shield to barrel. Since both shield and barrel are preferably made of a hard or rigid plastic material, such as styrene, sealing techniques compatible with plastic components are most suitably employed. In particular, the outer periphery 22 of needle shield 21 surrounding the distal end of the barrel is connected thereto at point 23 by fusing or joining the plastic material together such as by heating specific areas through spin welding techniques, laser welding, ultrasonic sealing, heat staking and other compatible methods. Peripheral element 22 is provided with a circular rib 24 which is engaged in a groove 25 on the distal end of the barrel to provide a mechanical interlock. In addition, one or more sterility rings 27 are included around the inner surface of the peripheral element; these rings are sized to contact the distal end of the barrel in virtually interference fit. The joining of the plastic materials, the mechanical interlock and the contacting sterility rings cooperate to provide a bacteria barrier to maintain the sterile or clean integrity of needle cannula 14.

As can be seen in FIGS. 1 and 2, the area where needle shield 21 and its larger peripheral portion 22 meet has a reduced wall thickness to form a frangible portion 26. The frangible portion is generally positioned in an intermediate region of the shield and may be formed by molding the preferably integrally fabricated shield with such a reduced thickness portion; scoring the area where shield and larger peripheral portion meet; undercutting or beveling this area of the shield; or other ways of providing a weakened stress section susceptible to rupture. It is noted when viewing these drawings that frangible portion 26 does not provide a hole or other leakage to the contents within the shield so that sterility or cleanliness would be compromised. In other words, the bacteria barrier is still maintained by this area of reduced wall thickness.

At the proximal end of barrel 11 a cap 30 is provided covering plunger 16. This cap is similar in most respects to cannula shield 21, particularly in the types of materials used and the manner in which the cap is connected to the barrel of the syringe, such as by heat sealing or ultrasonic sealing points 33. To this end, cap 30 includes a circular rib 31 which is engaged in a groove 32 at the proximal end of the barrel to provide a mechanical interlock, and one or more annular sterility rings 37 to contribute to the sterility barrier formed by the cap. In its preferred form, cap 30 is an integrally formed structure which includes a weakened section 34 in an intermediate region in the periphery of the cap, which serves as a frangible portion to separate the cap into two parts upon rupture of same. Once again, as in the case of the cannula shield, frangible portion 34 is preferably an area of reduced wall thickness which will allow the cap to become separated into two portions.

It can be seen that shield 21, barrel 11 and cap 30 all cooperate to form a package for the syringe, with the cleanliness or sterility of the package being provided by the sealed features of the shield and the cap to the barrel. It is to be understood that in the broadest application of this invention the cap need not include a breakable portion as particularly shown, although it is preferred. If the breakable portion is not included, the cap need only be otherwise removable.

FIG. 3 illustrates the opening of the syringe package of the present invention along with its advantageous features. Particularly, in order to expose needle cannula 14, frangible portion 26 is ruptured by the user by pushing, pulling or twisting shield 21. This action serves to rupture frangible portion 26 thereby separating the originally integral shield component into two portions. Shield 21 is removed, whereas peripheral portion 22 remains connected to barrel 11. Thus, this broken peripheral portion 22 serves as clear evidence to the user that the barrier seal has been broken, even when the shield has been removed. Since the shield cannot be reassembled or rejoined to assume its original form of integrity with the remaining peripheral portion 22, the user cannot be misled as to evidence of a broken barrier seal.

At the opposite end of the syringe, cap 30 is removed in substantially the same fashion as the shield in order to expose plunger 16. Frangible portion 34 is ruptured by pushing, pulling or twisting cap 30 so that the cap is removed, leaving a broken portion 36 still connected to the proximal end of barrel 11. Once again, these two separated components, one entirely removable, the other remaining connected to the barrel, provide a readily identifiable indicator that the barrel seal has been broken for access to the syringe. Reassembly of cap 30 to this end of the syringe cannot be performed to produce an integral cap component as originally fabricated.

As an additional feature to shield 21, internal ribs 38 are provided in the interior of the shield. These ribs mate with exterior ribs 15 on hub 12. Inasmuch as hub 12 and needle cannula 14 are preferably removable from the barrel, the interlocking relationship of the ribs in the shield and the ribs on the hub facilitate removal of the hub from the barrel. This is accomplished by a twisting action of the shield by the user who desires to remove the needle and hub assembly from the barrel.

In FIGS. 4 and 5, an alternative embodiment of the frangible portion of the shield is illustrated. In this embodiment of a syringe 40 a cannula shield 41 is connected to barrel 42. Both the shield and its manner of connection to the barrel are substantially similar to the embodiment described above. This shield, however, includes two frangible areas 44 and 45, such as core lines or undercuts, which define a band 46 in an intermediate region of the shield. A pull tab 48 is connected to and extends from the band section. To expose the needle cannula, the user grasps pull tab 48, and by pulling away, ruptures frangible portions 45 and 46 to thereby peel band 46 from the shield. Once the frangible portions are completely ruptured, shield 41 is removed from the syringe leaving a peripheral section 49 still connected to the barrel. While in the embodiment illustrated, particularly in FIG. 5, band 46 is shown completely separated from both shield 41 and peripheral section 49, this band may remain attached to the shield for its removal also. As in the previously described embodiment, peripheral portion 49 serves to indicate to a user that the barrier seal of the cannula shield has been broken. These broken components cannot be reassembled to form the integral structure as originally fabricated. Therefore, these features provide a tamper proof element to this syringe of the present invention.

While not illustrated, the cap at the proximal end of the barrel may include the same type of a peelable section of material defined by two frangible portions around the cap.

It should be pointed out that when the cannula shield or cap is joined to the barrel, the breaking stress of the frangible portions of the shield or the cap should be less than the bond strength of the connection between shield and cap to the barrel. In this way, the respective separable portions of the shield and the cap can remain connected to the barrel after the frangible portions have been ruptured. Otherwise, the entire shield or cap would be removed leaving no tamper proof evidence behind connected to the barrel for observation by the user that the barrier seal has been broken.

Thus, there has been provided in accordance with the principles of the present invention a syringe package which clearly indicates to a user that the seal to the cannula shield or plunger cap has been broken. The syringe package assembly is compact and is formed only by the exterior surface of the syringe barrel, the cannula shield and the plunger cap.

What is claimed is:
1. A syringe package comprising:
an elongated, hollow barrel;
a slidable plunger inside said barrel extending out of a proximal end of said barrel;
a needle cannula extending from a distal end of said barrel in fluid communication with the interior of said barrel;
a shield covering said cannula and connected to said barrel to provide a bacteria barrier, said shield having a frangible portion in an intermediate region thereof, whereby when the frangible portion is ruptured, a first portion of said shield is removable to expose said cannula and a second portion of said shield is adapted to remain connected to said barrel as evidence of a broken barrier; and
a cap covering the proximal end of said plunger and connected to said barrel to provide a bacteria barrier, said cap having a frangible portion in an intermediate region thereof, whereby when the frangible portion is ruptured a first portion of said cap is removable to expose said plunger and a second portion of said cap is adapted to remain connected to said barrel as evidence of a broken barrier.

2. The package of claim 1 wherein the breaking stress of said frangible portions of said shield and said cap is less than the bond strength of the connection between shield and cap to said barrel so that the respective second portions of said shield and said cap can remain connected to said barrel after rupture of the frangible portions.

3. The package of claim 1 wherein the frangible portions of said shield and said cap are areas of reduced wall thickness relative to the wall thickness of the remaining portions of said shield and said cap.

4. The package of claim 1 wherein said shield and said cap are made of plastic material.

5. The package of claim 1 wherein the frangible portion of one of said shield or said cap is a peelable section of material between said first and second portions which operates to separate said portions for removal of said first portion.

6. The package of claim 5 wherein both said shield and said cap include peelable sections of material between said respective first and second portions.

7. The package of claim 1 wherein said needle cannula is connected to said barrel by means of a hub which is removable from said barrel.

8. The package of claim 7 wherein said shield includes internal ribs and said hub includes mating ribs, both sets of ribs adapted to interlock with each other to facilitate removal of said hub with cannula from said barrel.

9. A syringe package comprising:
a hollow barrel;
slidable plunger means inside said barrel extending out of a proximal end of said barrel;
a needle cannula extending from a distal end of said barrel in fluid communication with the interior of said barrel;
a shield covering said cannula and connected to said barrel to provide a seal thereto;
frangible means associated with said shield adapted to be ruptured so that said shield is removable to expose said cannula with means remaining connected to said barrel for indicating evidence of a broken seal; and
a removable cap covering the proximal end of said plunger with only said shield, cap and barrel exterior providing a package for the syringe.

10. A syringe package comprising:
an elongated, hollow plastic barrel;

a slidable plunger inside said barrel extending out of a proximal end of said barrel;

a needle cannula extending from a distal end of said barrel in fluid communication with the interior of said barrel;

a plastic shield covering said cannula and connected to said barrel to provide a bacteria barrier, said shield having a frangible portion in an intermediate region thereof formed by a reduced wall thickness relative to the wall thickness of the remaining portions of said shield, whereby when the frangible portion is ruptured a first portion of said shield is removable to expose said cannula and a second portion of said shield is adapted to remain connected to said barrel as evidence of a broken barrier; and a plastic cap covering the proximal end of said plunger and connected to said barrel to provide a bacteria barrier, said cap having a frangible portion in an intermediate region thereof formed by a reduced wall thickness relative to the wall thickness of the remaining portions of said cap whereby when the frangible portion is ruptured a first portion of said cap is removable to expose said plunger and a second portion of said cap is adapted to remain connected to said barrel as evidence of a broken barrier.

* * * * *